United States Patent [19]
McConnell et al.

[11] Patent Number: 5,874,477
[45] Date of Patent: Feb. 23, 1999

[54] METHOD OF TREATMENT FOR MALARIA UTILIZING SEROTONIN RECEPTOR LIGANDS

[75] Inventors: Bruce McConnell, Albuquerque, Ariz.; Christopher P. Locher, San Francisco, Calif.

[73] Assignee: The University of Hawaii, Honolulu, Hi.

[21] Appl. No.: 289,379

[22] Filed: Aug. 12, 1994

[51] Int. Cl.[6] .................................................. A61K 31/135
[52] U.S. Cl. .......................... 514/657; 514/895; 514/452; 514/289; 514/415; 514/392
[58] Field of Search .................................. 514/657, 895, 514/452, 289, 415, 392

[56] References Cited

U.S. PATENT DOCUMENTS 5,021,426  6/1991  Badwin et al. ........................ 514/313

OTHER PUBLICATIONS

Agarwal, et al, Chemical Abstracts, vol. 14, No. 2. pp. 237–245 (1993) "3–D QSAR for intrinsic activity of 5–HT1A receptor ligands by the method of comparative molecular field analysis", abstract No. 118:204695, J. Comput. Chem., 14(2), pp. 237–245.

Harrington, et al. Medline Abstracts, vol. 268. No. 3, pp. 1098–1106 (1994) "Agonist–induced Desensitization and loss of high–affinity binding sites of stably expressed human 5–HT1A receptors", abstract No. 94186960, J. Pharmacol. Exp. Ther., 268(3), pp. 1098–1106.

Ryall, J.C. "Reversal of Chloroquine Resistance in Falciparum Malaria," Parasitology Today, vol. 3, No. 8, 1987, p. 256.

Bitonti, Alan et al., "Reversal of Chloroquine Resistance in Malaria Parasite Plasmodium Falciparum by Desipramine," Science, vol. 242, pp. 1301–1303, 1988.

Kyle, Dennis E., et al., "Plasmodium falciparum: modulation of calcium antagonists of resisting chloroquine, desethylchloroquine, quinine and quinidine in vitro," Transactions of the Royal Society of Tropical Medicine and Hygiene, (1990) 84, 474–478.

Chemical Abstracts AN 1989:420769, Tanabe et al.

Chemical Abstracts AN 1987:78455, Adachi et al.

Medline Abstract: Harrington–MA, et al, "Agonist–induced desensitization and loss of high–affinity binding sites of stably expressed human 5–HT1A receptors", J. Pharmacol.–Exp–Ther. 268(3) pp. 1098–1106, Mar. 1994 (Abstract only).

Chemical Abstract 118:204695 Agarwal et al, "3–D QSAR for intrinsic activity of 5–HT1A receptor ligands by the method of comparative receptor field analysis", J. Comput. Chem. 14(2), 1993, 237–45.

*Primary Examiner*—Keith D. MacMillan
*Attorney, Agent, or Firm*—Gray, Cary, Ware & Freidenrich, LLP; Stephen E. Reiter; David F. Kleinsmith

[57] ABSTRACT

The invention provides a method of preventing or treating malaria comprising administering a therapeutically effective amount of serotonin receptor ligand to reduce the pathological consequences of malaria infection in a patient, said serotonin receptor ligand characterized by an ability to displace an identifying ligand which defines the serotonin receptor subtype 5HT1a or 5HT2/5HT1c.

In addition, the invention provides a method of identifying a serotonin receptor ligand capable of reducing the pathological consequences of malarial infection in a patient comprising the step of sequentially assaying potential ligands to identify a ligand characterized by an ability to displace an identifying ligand which defines the serotonin receptor subtype 5HT1a or 5HT2/5HT1c.

14 Claims, 1 Drawing Sheet

METHOD OF TREATMENT FOR MALARIA UTILIZING SEROTONIN RECEPTOR LIGANDS

FIELD OF THE INVENTION

The present invention relates to a method of treatment for malaria and more specifically to a method of administering compounds to patients to inhibit the growth of the malaria parasite.

BACKGROUND OF THE INVENTION

Malaria is a global problem affecting over 200 million people each year. It is the cause of approximately four million deaths annually, mostly children, in developing countries. Although it was common in the southern states before World War II, malaria has been effectively eliminated in the United States. It now occurs most often in tropical and subtropical countries and also in temperate regions during the summer months. The disease is most prevalent in Africa, Southeast Asia and Latin America. However, malaria is not just a problem for the developing countries in which it occurs. It is an impediment to world development as it affects tourism and trade.

Human malaria can be caused by one of four known parasites: *Plasmodium ovale, Plasmodium malariae, Plasmodium vivax*, and *Plasmodium falciparum*. Although *Plasmodium vivax* is the most common cause of the disease, *Plasmodium falciparum* causes the most deadly form. *Plasmodium falciparum* is transmitted by the saliva of an infected female Anopheles mosquito. When an Anopheles mosquito bites a patient with malaria it sucks up blood cells containing malaria parasites. The parasites develop and multiply in the mosquito's stomach and them move into its salivary glands. When the malaria-infected mosquito infects sporozoites in its saliva, they migrate first to the liver where they replicate in hepatocytes, then they migrate through the bloodstream and infect red blood cells. This is called the liver-stage and is responsible for recurrent infections. When the mosquito bites again, it injects saliva containing the parasites. The parasites enter the victims red blood cells, complete their life cycle and then burst the blood cell causing the characteristic anemia and fever as the body tries to fight the foreign invasion. Infected individuals initially suffer from aches, fever, nausea and often vomiting. Symptoms of mild cases include drenching sweats and shaking chills, followed by months or even years of anemia and periodic fevers. Children infected with a *P. falciparum* can die within a few days after the first symptoms as ravaged blood cells clog capillaries and deprive the brain of oxygen.

Several approaches have been used in attempting to control the spread of malaria. One approach is to eliminate mosquito reproduction by draining the swamps and marshes where they reproduce or spraying the breeding grounds with oil or chemicals that destroy the larvae. However, draining or spraying disease infested swamps and marshes is impractical in many parts of the world and finding every swamp and marsh is impossible.

Much effort has focused on developing effective methods for killing the infected adult mosquitoes with insecticides. Studies of the habits of mosquitoes have shown that many types of mosquitoes bite only when they are indoors at night. Immediately after biting, they seek rest on a nearby surface. Spraying the walls and ceilings of indoor rooms with insecticides such as DDT and dieldrin, which remain active for a long time, has been somewhat effective in reducing the incidence of malaria. However, it is clear that mosquitoes are developing resistance to the pesticides being used.

Defense forces from Australia, the U.S. and Canada have tested clothes which have been treated with the insecticide Perigen to protect the wearer from mosquitoes or other insects that feed on blood. Although undergarments may be worn to protect the skin from the insecticide on the clothes, it is thought that the long term effects of the pesticide so close to the human body may be worse than the risks of malaria. In addition, there remains the growing problem of mosquito resistance to insecticides.

Another approach to preventing the spread of malaria is the use of chemotherapy drugs to kill the parasite in a patient. Many different drugs have been used to prevent and/or treat malaria, including quinine, atabrine, chloroquine, mefloquine, and primaquine. The drugs work in the patient by killing the parasite at various stages of its life cycle. However, parasite resistance to some drugs is an increasingly serious problem. Resistance is often due to mutation of the parasites' proteins. Researchers at John Radcliffe Hospital in Headington, England, have found the mutation rate in *P. falciparum*, for example, is 2% per generation. Mutation of surface proteins may help the parasites avoid the immune system of their victims and makes it difficult to develop vaccines. Scientists predict that since malaria parasites are becoming resistant to all known drugs, malaria may be untreatable in the near future.

There are serious drawbacks to the use of many existing anti-malaria drugs because of the side effects they produce in patients. For example, chloroquine can cause gastrointestinal disturbances, visual disturbances, irreversible damage to the retina, skin reactions, hair loss and hair depigmentation. Furthermore, chloroquine must be used with caution, if at all, in patients with hepatic and renal impairment and may be contra-indicated in patients with psoriasis, epilepsy and other neurological conditions.

Another drug with serious side effects is Artemether (Paluther) which is used for the treatment of acute outbreaks of quinine resistant malaria. Artemether is based on a semi-synthetic derivative of an ancient Chinese herbal pharmaceutical and has the severe drawback of being associated with fatal neurotoxicity.

There may be hope for the use of antisense drugs that limit the growth of the parasite in patients, however research in this area has not progressed sufficiently for antisense drugs to be considered an imminent solution to the problem.

Scientists have predicted that global warming may bring an onslaught of diseases, such as malaria, the plague, yellow fever and others. The interrelated consequences of global warming, increased worldwide travel, and the current epidemic of drug resistant malaria parasites have created an urgent need for effective and safe drugs to treat and prevent the lethal or debilitating symptoms associated with the malaria parasite. The present invention satisfies this need and provides related advantages as well.

SUMMARY OF THE INVENTION

The aforementioned limitations and others have been eliminated by the present invention which provides a method for treating malaria which reduces or circumvents the problems of mosquito resistance, parasite resistance and toxic side effects inherent in the previously known methods. The method of the present invention has the additional advantage of using compounds that are cheaply made and chemically stable. In Third World countries, chemical precursors of the compounds can be obtained from recycled natural sources such as fruit peelings.

The present invention is predicated on the unexpected discovery of anti-malarial activity of low molecular weight compounds of several diverse molecular classes sharing the property of acting as active ligands to several subtypes of receptor for brain serotonin (5-hydroxytryptamine or 5HT). Serotonin is a well characterized neurotransmitter which regulates calcium ion channels on the surface of nerve and muscle cells. Some serotonin receptor ligands are clinically approved as drugs for the treatment of migraine headaches, depression, high blood pressure, and psychosis. The present invention provides a novel method of using serotonin receptor ligands in the prevention and treatment of malaria.

The invention provides a method of preventing or treating malaria comprising the administration of a therapeutically effective amount of serotonin receptor ligand to reduce the pathological consequences of malaria infection in a patient, said serotonin receptor ligand further characterized by an ability to (a) displace an identifying ligand which defines the serotonin receptor subtype 5HT1a or 5HT2/5HT1c, (b) function as an active ligand when bound at said serotonin receptor subtype site, and (c) cause growth inhibition of the malaria parasite.

In addition, the invention provides a method of identifying a serotonin receptor ligand capable of reducing the pathological consequences of malarial infection in a patient comprising the step of sequentially assaying potential ligands to identify a ligand characterized by an ability to (a) displace an identifying ligand which defines the serotonin receptor subtype 5HT1a or 5HT2/5HT1c, (b) function as an active ligand when bound at said serotonin receptor subtype site and (c) cause growth inhibition of the malaria parasite.

DETAILED DESCRIPTION OF THE PREFERRED EMBODIMENTS

Figure 1:
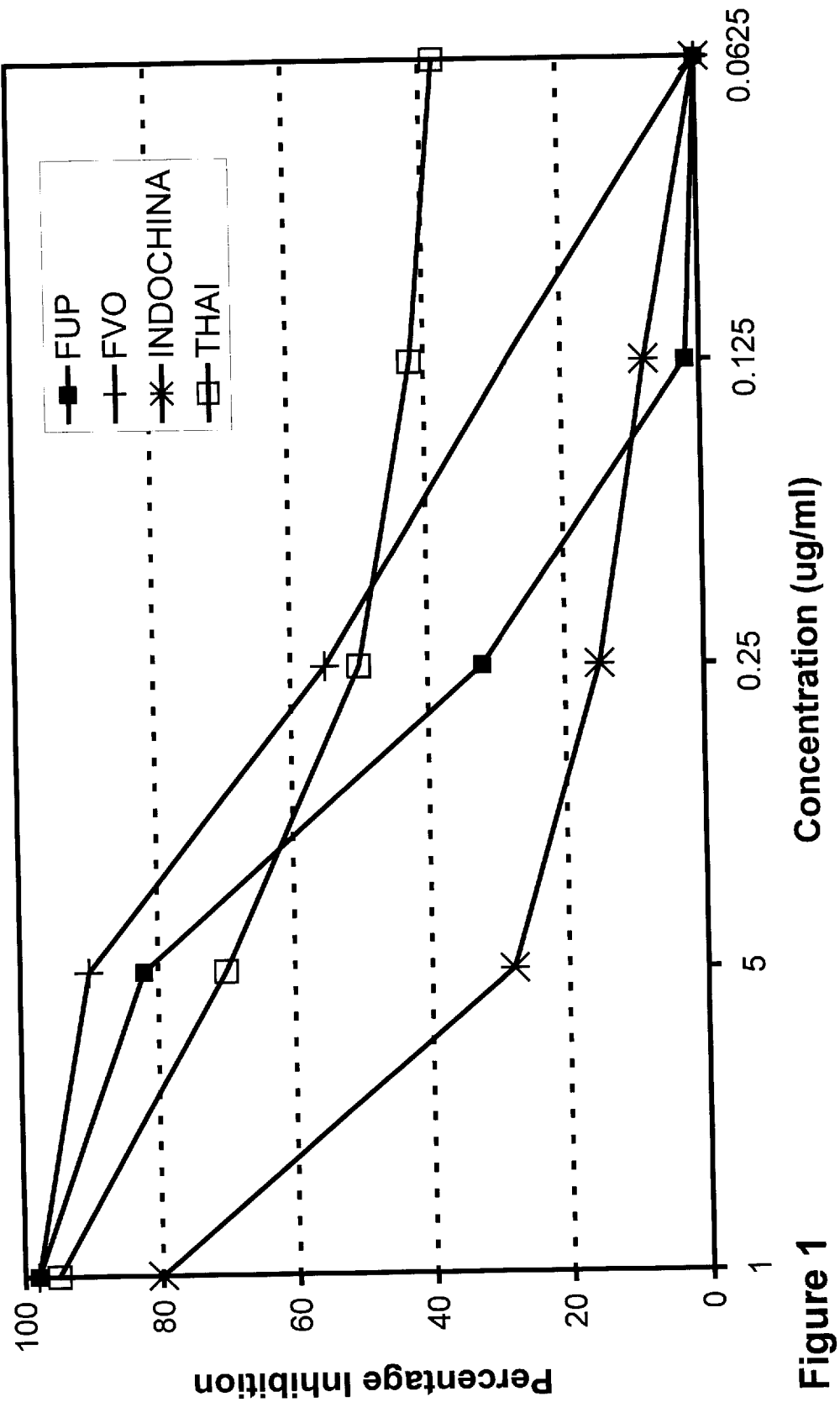
FIG. 1 shows the growth inhibitory effect of a serotonin receptor ligand, 8-OH-DPAT, on four *P. falciparum* isolates.

The invention provides a method of using ligands to serotonin receptor subtypes 5HT1a, 5HT2 (a and b) and 5HT1c as chemotherapeutic and prophylactic agents against malaria. The ligands are administered orally or injected in such a manner as to attenuate and prevent malaria symptoms, for example, by arresting the life cycle of the malaria parasite within the patient, decreasing the production of malarial parasite DNA, or decreasing the severity of malaria symptoms in the patient. The compounds of the invention can be used either as the free base or as the pharmaceutically acceptable acid-addition salt form, for example, hydrochloride, hydrobromide, and tartrate maleate. They may be used in oral or injectable pharmaceutical preparations as prophylactic- and acute phase-remedies for the relief and reversal of malaria symptoms. They may be used alone or in combination with each other or other known anti-malarials. Many of the compounds used in the present invention are associated with rapid tolerance of possible side effects that would permit the administration of a low initial dose, followed by repeated larger doses without psychological effects. These compounds are completely devoid of addictive potential and, judging from their anti-malarial potency, might be used at dosages below threshold for psychological side effects and toxicity.

As used herein, the term "patient" refers preferably to a human patient, however, the invention also has veterinary applications and may be used to treat any animal susceptible to other species of malaria, for example, birds, lizards, and monkeys.

Ligands to the 5HT1a, 5HT2 (a and b) and 5HT1c subtype receptors are referred to as 5HT1a, 5HT2 (a and b) and 5HT1c ligands. They are defined as any chemical compound, regardless of molecular structural type, that exhibits clearly measurable binding competition against established identifying serotonin receptor ligands that are documented to define 5HT1a, 5HT2 (a or b) or 5HT1c receptor subtypes by their selectivity and high affinity. This applies to receptor preparations derived from any biological source.

As used herein, the term "ligand" applies to any identifying compound or ligand or their competitors and includes, but is not necessarily limited to the functional categories of agonist, partial agonist and antagonist. An "agonist" is defined as a ligand that promotes the normal biological function of the receptor when it competes successfully with the normal endogenous ligand (5HT) for binding to the receptor. A "partial agonist" binds as does the agonist, but promotes only partial receptor function. An "antagonist" inhibits all receptor function with its binding to the receptor in competition with the normal, endogenous agonist.

Receptors of the type included here are mediators of biological activity, notably calcium mobilization at a cell membrane associated with modulation of the functional activity (activation or suppression) of specialized cells. With its binding to a receptor a ligand modulates this activity in three ways, either as an agonist (binding and promoting activity), a partial agonist (binding with partial activity) or an antagonist (binding and inhibiting activity). These activities are measured by the biochemical detection of the production of inositol phosphates or nucleotide cyclic phosphates in tissue preparations (Kendall, D .A. and Hill, S .J. in "Methods in Neurotransmitter Analysis" H. J. Yamamura, S. J. Enna and M. J. Juhar, eds Raven Press, N.Y. pp. 69–88 and Strada, S. J., Duman, R. S. and Enna, S. J. Op. Cit.).

An identifying ligand always has a very high affinity (0.1 to 10 nanomolar dissociation) and is often, but not always an antagonist. Since these are usually radiolabeled for purposes of the binding assay, they are often referred to as radioligands. Thus, for purposes of simplifying further technical discussion, "identifying radioligand" or "radioligand" will be used synonymously with receptor subtype identifying compound.

The serotonin receptor subtypes as defined by their established identifying ligands are as follows:

5HT1a, any receptor that shows exclusive, high affinity to the agonist 8-hydroxy-DPAT (8-hydroxy-2-(di-n-propylamino)-tetralin) as an identifying ligand. Other high-affinity ligands selective for the 5HT1a receptor exist, for example, ipsapirone, WB-4101 and 5-methoxy-N, N-dimethyltryptamine. All of these compounds will bind to 5HT1a with dissociation constants of <10 nM (nanomolar).

5HT2 (a and b), any receptor that shows high (<10 nM) affinity for the antagonist, ketanserin as an identifying ligand for this receptor. Additional ligands that can be used as high affinity definers, but with less selectivity are: cinanserin, spiperone, ritanserin, pirenperone and chlorpromazine. An agonist that selectively defines the 5HT2a receptor is (−) DOB (2,5-dimethoxy-4-bromophenyl-n-propylamine).

5HT1c, any receptor that shows a similar high-affinity binding pattern to that of 5HT2 with the 5HT2 (a and b) ligands listed above, but with no highly selective ligands.

The aforementioned identifying ligands which define a particular serotonin receptor subtype show receptor subtype selectivity, but must qualify as such by having a dissociation constant less than 10 nanomolar. Thus, while both ketanserin and spiperone (5HT2 identifying compounds) can be shown to bind to 5HT1a receptors, they do not qualify as identifying ligands for the 5HT1a, owing to a dissociation constant between 10 and 1000 nM for 5HT1a. The definition of any chemical compound as an anti-malarial will be established by the ability of this compound to compete with any subtype-identifying compound as defined above for its binding site to any 5HT receptor preparation and thus qualify as a ligand and anti-malarial, regardless of whether the actual functional receptor in anti-malarial activity can or cannot be established unequivocally as 5HT1a, 5HT2 (a or b) or 5HT1c, subsequently. While any compound displacing a radioligand from the receptor with medium or high affinity qualifies as a ligand, its qualification as an anti-malarial candidate through further demonstration of its possible agonist, partial agonist or antagonist activity is supportive, but not necessary.

Thus, anti-malarial activity is related to a compound's affinity for these 5HT receptor subtype sites, i.e. the ability to compete with any subtype-identifying compound, rather than to its actual function as agonist or antagonist at 5HT receptor subtype site. It should be recognized that the 5HT receptors operating in any anti-malarial system involving erythrocytes and parasites could differ subtly or grossly from the well established receptor subtypes in regard to their patterns of binding to several ligands. A binding assay to qualify a new compound as an anti-malarial would involve detection of the compound's competition with a subtype-identifying compound as indicated by a decrease in radioligand remaining on a washed filter or in a washed centrifuged pellet in a sample. The sample is obtained after preincubation of a 5HT receptor preparation with a putative anti-malarial ligand in the presence of the identifying radioligand. Such binding assays have indicated that 8-hydroxy-DPAT and 5-methoxy-N, N-dimethyltryptamine (DMT) are identifying ligands for the 5HT1a serotonin receptor subtype and ketanserin and spiperone are identifying ligands for the 5HT2 (a or b) and 5HT1c receptor subtypes.

The invention provides for use of both the identifying ligands and other ligands capable of competing with them. The ligands of the invention can be classified into groups based on their potency in an anti-malarial assay, their selectivity and affinity in the binding assay. "Preferred" ligands refers to ligands with high potency in the anti-malarial assay, i.e. an activity at concentrations of less than 1 μg/ml. "Selective" ligands refers to ligands with exclusivity of receptor subtype binding. "Non-selective" ligands can bind to more than one receptor subtype. "High-", "medium-" or "low-affinity" ligands refers to ligands with receptor dissociation constants of <10 nM, 10–1000 nM and >1000 nM, respectively.

The compounds used in the invention are chosen from several groups of serotonin receptor agonists, partial agonists and antagonists. In one embodiment, the compounds are 5HT1a receptor agonists, such as amino tetralins, having the general structure:

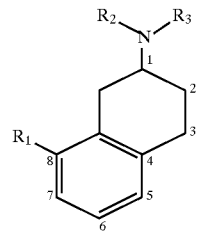

Wherein:
R$_1$=OH, O—CH$_3$, O—Ph, O-alkyl or O-aryl groups;
R$_2$=H, O—CH$_3$, n-propyl, an aryl or alkyl group; and
R$_3$=H, n-propyl, an aryl or alkyl group, (CH$_2$)$_3$—Ph or phthalyl, i.e., the (n-phthalylimido) butyl group.

In another embodiment, the compounds of the invention are chroman derivatives of amino tetralins where carbons 1 and 3 above are replaced by an endocyclic oxygen, R$_1$=O—CH$_3$, R$_2$=R$_3$=n-propyl.

Another embodiment of the invention includes use of phenyl dioxin such as:

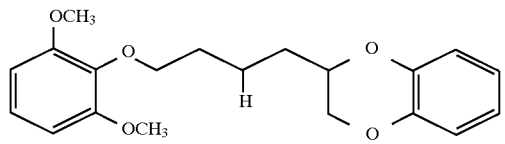

Another embodiment of the invention includes the use of compounds that are both 5HT1a and 5HT2 agonists, for example, ring substituted phenylalkylamines of the general structure:

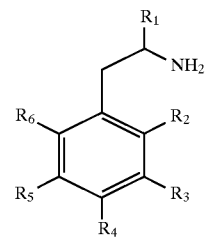

Wherein:
R$_1$=H or CH$_3$;
R$_2$=H or O—CH$_3$;
R$_3$=H or O—CH$_3$;
R$_4$=CH$_3$, O—CH$_3$, I, Br, S—(CH$_2$)$_2$—CH$_3$, or is involved in a cyclic methylenedioxy group with R$_5$;
R$_5$=O—CH$_3$, S—CH$_3$, or is involved in a cyclic methylenedioxy group with R$_4$; and
R$_6$=H or O—CH$_3$ In another embodiment, the compounds used in the invention are any other combination of methoxy, ethoxy or methylene dioxy ring substituents with or without additional 4-position substituents that would include alkyl, aryl, alkyl sulfur, or halogens forming ligands that can bind to 5HT2/5HT1a receptor subclasses with high or medium affinity.

In another embodiment, the compounds of the invention are ergolines of the general structure:

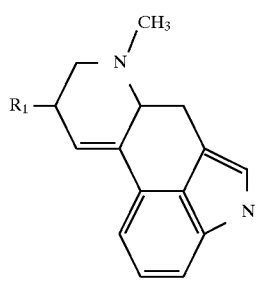

Wherein:

R$_1$=diethylamide, N—(C=O)—N(Et)$_2$, or N—(C=O)—O—CH$_2$—Ph.

In still another embodiment the compounds used in the invention are partial ergolines of the general structure:

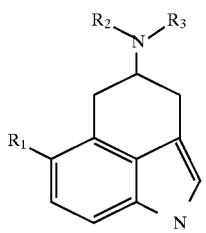

Wherein:

R$_1$=OH or O—CH$_3$;
R$_2$=H or n-propyl; and
R$_3$=n-propyl or alkyl.

In another embodiment the compounds of the invention are tryptamine derivatives, both selective and non-selective, of the general structure:

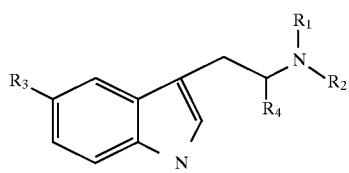

Wherein:

R$_1$=H, n-propyl, or CH$_3$;
R$_2$=H, n-propyl, CH$_3$;
R$_3$=OH, O—CH$_3$, or —(C=O)—NH$_2$; and
R$_4$=H or CH$_3$.

In another embodiment, the compounds of the invention are indole derivatives of the general structure:

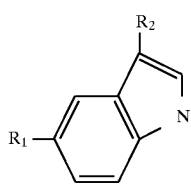

Wherein:

R$_1$ = O—CH$_3$ and

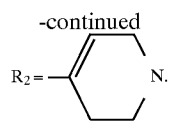

In another embodiment the compounds of the invention are anhydro indolquinolines having the general structure:

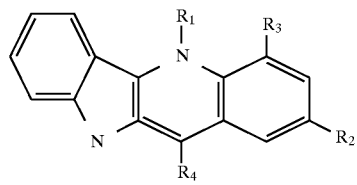

Wherein

R$_1$=H or alkyl (e.g., methyl) or no substituent with full ring unsaturation

R$_2$=methoxy or chloro

R$_3$ = H or NH—CHCH$_2$CH$_2$CH$_2$NH$_2$
                    |
                    CH$_3$

R$_4$ = H or NH—CHCH$_2$CH$_2$CH$_2$N(C2H5)$_2$
                    |
                    CH$_3$

Additional 5HT1a receptor agonists which may be used in the invention include arylpiperazines of the general structure:

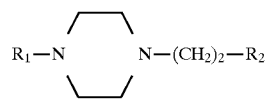

Wherein:

R$_1$ = 2-pyrmidyl,

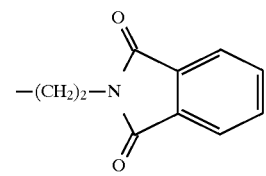

R$_2$=Ph—NH$_2$, 6[CH$_2$—N—]—1,3-dimethyluracil, 6[CH$_2$—N]—1,3-dimethylthymine, or Examples of arylpiperazines useful in the invention are adrenergic antagonists, urapidils, and ipsapirone.

Additional 5HT1a/5HT2 agonists which may be used as compounds of the invention include, adrenergic blockers such as aryloxyalkylamines of the general structure:

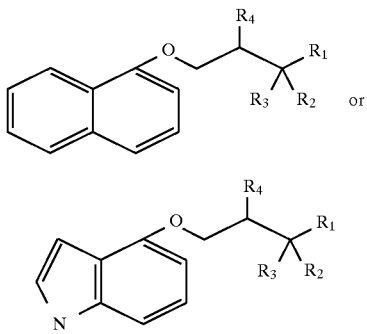

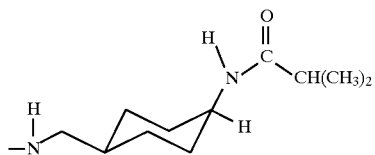

Wherein:

$R_1$=N(Et)$_2$, N-(dialkyl), diethylamine or

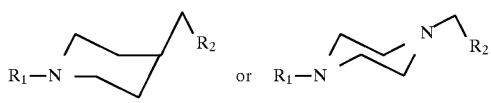

$R_2$=H or CH$_3$;

$R_3$=H or CH$_3$; and $R_4$=H or OH.

In another embodiment the compounds of the invention include high-affinity ligands for the 5HT1a receptor that are also α, β or Δ adrenergic antagonists, including: WB 4101, yohimbine, rauwolscine, idazoxan, urapidil, N-methylquipazine and quipazine.

In other embodiments, the compounds of the invention include 5HT2 antagonists. These compounds define the 5HT2 receptor subtype and include ketanserin, ritanserin and spiperone, all of which exhibit anti-malarial activity, in line with general observations that non-specific 5HT1a ligands can produce agonistic biological effects, even as antagonists of another subtype, the (5HT2) receptor.

Examples of 5HT2 antagonists which are useful in the invention include alkyl piperadines and alkylpiperazines of the general structure:

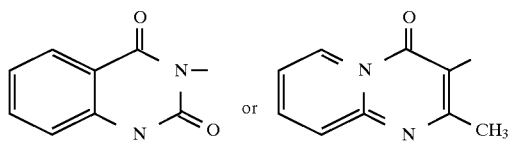

Wherein:

$R_1$=a fused, heterocyclic aromatic ring system, e.g.,

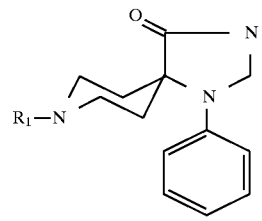

$R_2$=a parafluorobenzoyl group or similar fused heterocyclic aromatic ring system, an imidazole, or hydroxyl group.

In another embodiment the compounds of the invention are alkylpiperadines of the general structure:

Wherein:

$R_1$=a benzalkylparafluoro or a 7-benzodioxin group. (Glennon, R. A., Westkaemper, R. B. and P. Bartyzel, in "Serotonin Receptor Subtypes: Basic and Clinical Aspects," S. J. Peroutka, ed. Wiley-Liss (1991) pp 19–64 and Peroutka, S. J., in "Serotonin Receptor Subtypes: Basic and Clinical Aspects," S. J. Peroutka, ed. Wiley-Liss pp 65–80.)

The following examples are intended to illustrate but not limit the invention. While they are typical of those that might be used, other procedures known to those skilled in the art may be alternatively employed.

Experimental Disclosure

In the experimental disclosure which follows, all weights are given in grams (g), milligrams (mg), micrograms (μg), nanograms (ng), picograms (pg) or moles (mol); all concentrations are given as percent by volume (%), molar (M), millimolar (mM), micromolar (μM), nanomolar (nM), picomolar (pM), normal (N); all volumes are given in liters (l), milliliters (ml) or microliters (μl); and all lengths are given in millimeters (mm) or nanometers (nm), unless otherwise indicated. Standard abbreviations are used for chemical compounds except that Ph=phenyl and Et=ethyl.

EXAMPLE I

Assaying the Ability to Displace a Primary Ligand

The definition of active 5HT1 and 5HT2 ligands is based primarily on the ability of a compound to displace a high-affinity, selective radioactively labeled ligand (referred to here as a radioligand or identifying ligand) that defines the receptor subtype (ketanserin for 5HT2 and 8-hydroxy DPAT for 5HT1a) in washed homogenates of rat brain frontal cortex membrane receptor preparations. The radioligand and the unknown ligand are mixed in pH 7.6 buffer containing the cortical receptors representing several serial dilutions of the test compound. After 15 min incubation at 37° C. suspended membrane particulates are separated from the suspension by filtration (or centrifugation), washed, dried and transferred to a scintillation vial for counting. Plots of fraction bound (CPM minus background/maximum CPM minus background) against concentration of unknown are compared with plots for a known ligand. Quantitative estimates of the ligand's binding affinity (dissociation constant) and maximum binding are obtained by a non-linear least squares fitting of the experimental data from the model, $$\text{Fraction bound} = \frac{B_{max}(k)}{K_k[1 + L/K_L] + k}$$

where $B_{max}$ is the maximum binding, k is the concentration of radioligand, $K_k$ the radioligand dissociation constant, $K_L$ is the unknown ligand concentration and $K_L$ is its dissociation constant. The most effective of the anti-malarials tested show $K_L$ values in the 0.2 to 10 nM range for 5HT1a receptor agonists and in the 10 to 500 nM range for 5HT2 receptor agonists. 5HT2 receptor antagonists such as ketanserin and spiperone have $K_L$ values between 0.25 and 1 nM. Some ligands, such as the ergolines show low selectivity (bind to several subtypes) with high affinity (≈1 nM) to both 5HT1a and 5HT2 (McKenna, D. J., and Peroutka, S. J., J. Neurosci. 3482–3490 (1989).

EXAMPLE II

Assaying the Ability to Function as a Ligand

Once ligand binding and serotonin receptor subtype specificity have been determined, the ability to function as an agonist, antagonist or partial antagonist can be evaluated by activation of adenylate cyclase. This is determined by measuring the amount of cyclic adenosine monophophate (cAMP; pmol/mg protein) induced by serotonin in synaptosomal membrane-enriched fractions using a radioimmunoassay (Fillion et al, 1979. Life Sciences, 24:1813–1822). Briefly, samples are incubated for 2 minutes at room temperature in 50 mM TRIS-HCl buffer, pH 7.4 containing 0.5 mM EDTA, 0.4 mM ATP, 2.0 mM MgSO4 and 1.0 mM isobutyl methylxanthine and the reaction is stopped by boiling and the addition of ⅕ volume ethanol. The supernatant is collected, lyophilized and resuspended in 0.1 ml of sodium acetate buffer, pH 6.2. An equal volume of iodinated tracer (10,000 dpm) and rabbit anti-cAMP (diluted to 50% binding of labeled antigen) is added and the samples are incubated overnight. 50 ul of 1% bovine serum albumin and 1 ml of cold ethanol is added and the samples are centrifuged at 2200×g for 15 minutes. Sample pellets are collected and counted using a gamma spectrometer.

EXAMPLE III

Anti-malarial Assay

Anti-malarial activity of compounds such as quinine or chloroquine can be demonstrated by an in vitro assay involving human erythrocytes and the human malaria parasite, *Plasmodium falciparum*. Human red blood cells were infected with the malarial parasite in culture and synchronized to eliminate all but the cells infected with the ring-stage of the malaria life cycle. The trial anti-malarial was added to the medium in at least three triplicate concentrations using sterile technique. After a four day incubation at 37° C. under specific gas mixtures of 90% $N_2$, 8% $CO_2$, and 2% $O_2$, DNA synthesis was measured by the amount of radioactive hypoxanthine incorporated into acid-insoluble material. Typical CPM for normal DNA synthesis without anti-malarial is ≈2500 CPM, compared to ≈25 CPM in the presence of 0.1 μg/ml of chloroquine. (Desjardins, el al., in *Anti-malarial Agents and Chemotherapy*, pgs. 710–718 (1979)).

Seven serotonin receptor ligands were evaluated along with serotonin for growth inhibition of *P. falciparum* (Table 1). Three serotonin receptor agonists showed marked growth inhibition, while three serotonin receptor antagonists showed marginal but significant growth inhibition. Serotonin showed no growth inhibition.

TABLE I

| SEROTONIN RECEPTOR LIGAND | RECEPTOR SPECIFICITY | LIGAND FUNCTION | 50% PARASITE GROWTH INHIBIT.[1] CONC. OF LIGAND $IC_{50}$[2] (μg/ml) | CPM's |
|---|---|---|---|---|
| 8-hydroxy DPAT(1)[3] | 5HT1a | Agonist | 0.125 | 900 |
| DOI(9)[4] | 5HT2 | Agonist | 0.250 | 2055 |
| 2C-B(9)[5] | 5HT2 | Agonist | 0.500 | 1678 |
| Serotonin | 5HT1a,5HT2, a,b,c | Agonist | >10 | (>4000) 0 |
| Spiperone | 5HT2, 5HT1a | Antagonist | 1.25 | 2591 |
| Ritanserin | 5HT2 | Antagonist | 2.50 | 2913 |
| Ketanserin | 5HT2 | Antagonist | 5.00 | 1592 |
| DMT[6] | 5HT2 | Agonist | ≥10 | (>4000) 0 |

1. % inhibition = $\frac{\text{test compound CPM} - \text{background CPM}}{\text{control CPM} - \text{background CPM}}$
where Control CPM (from 3 wells w/o drug) = 3977 CPM
Background CPM = 48 CPM.
2. $IC_{50}$ - concentration that causes 50% of $_3$H-thymidine uptake in control cultures (wells).
3. 8-hydroxy DPAT or 8-OH DPAT = 8-hydroxy-N-(di-n-propyl)aminotetralin.
4. DOI = 2,5-dimethoxy-4-iodoamphetamine.
5. 2C-B = 2,5-dimethoxy-4-bromophenethylamine.
6. DMT = dimethyltryptamine.

Minimal inhibitory concentrations of 8-OH-DPAT were determined for four *P. falciparum* strains, three of which were chloroquine resistant strains (FIG. 1).

The 5HT1a serotonin receptor agonist 8-OH-DPAT did not function additively or synergistically with serotonin receptor 5HT2 agonist DOI nor with 5HT2 antagonists ketanserin, ritanserin or spiperone, indicating that the relevant receptor functioning in the parasite/erythrocyte system is related to only one serotonin receptor subtype (not shown).

To determine if these serotonin receptor ligands functioned synergistically with chloroquine, a dose-dependent experiment was conducted using chloroquine sensitive and chloroquine resistant *P. falciparum* isolates. Two serotonin receptor agonists and two serotonin receptor antagonists markedly enhanced both parasite isolates sensitivity to chloroquine (Table 2).

TABLE 2

Synergism with Chloroquine of Serotonin Receptor Agonists and Antagonists on Growth Inhibition of *P. falciparum* (mean $^3$H-Hypoxanthine Radioactive counts)

| COMPOUND | CONTROL | CHLQ 32 pM | CHLQ 64 pM |
|---|---|---|---|
| EXPERIMENT 1 | | | |
| N/A | 9530 | 9202 | 2955 |
| DPAT | 8365 | 3778 | 262 |
| EXPERIMENT 2 | | | |
| N/A | 6975 | 4049 | 1317 |
| DOI | 6682 | 3228 | 167 |
| KETANSERIN | 6315 | 4497 | 1525 |
| SPIPERONE | 7416 | 3515 | 573 |

To quantitate the physiological response of malaria parasites to serotonin receptor (5HT1a and 5HT2) ligands, a patch-clamp technique can be used to (1) identify and locate the actual receptor within a lysis preparation consisting of the parasite membrane and the parasitophorous vacuole membrane (PVM), a remnant of the invaginated erythrocyte membrane that encloses the parasite; (2) characterize the basis of the parasite's physiological response to 5HT1a and 5HT2 agonists; (3) characterize the transport properties of these receptors and ascribed a functional definition, i.e., nutrient permeable channel (Desai, et al., *Nature,* Vol. 362, pg. 643, Apr. 15, 1993); and (4) identify the mechanism of action of serotonin receptor ligands on the malaria parasite, i.e., agonist or antagonist.

The "patch clamp" technique, which characterizes ion channels on cell surfaces, was employed to demonstrate the presence of a serotonin-like receptor on the surface of the malaria parasite and to define the mechanism of action of the anti-malarial compounds. This receptor was completely inhibited by 8-OH-DPAT at a concentration of 2 μg/ml (not shown).

In summary, of seven serotonin receptor ligands tested, the non-hallucinogenic 8-OH-DPAT (5HT1a agonist) showed the most marked growth inhibition of *P. falciparum* in vitro. The 5HT1a ligands known as selective agonists are the most potent of the anti-malarials defined in this invention, while both 5HT2 agonists and antagonists also show anti-malarial activity. The serotonin receptor ligands bind to a serotonin-like receptor present within the parasite-PVM membrane preparation, as demonstrated by patch-clamp. Some of the ligands can function synergistically with chloroquine and other serotonin receptor ligands.

Although the invention has been described with reference to the presently-preferred embodiments, it should be understood that various modifications can be made without departing from the spirit of the invention. Accordingly, the invention is limited only by the following claims.

We claim:

1. A method of treating malatia in a patient in need thereof, said method consisting essentially of administering to said patient a therapeutically effective amount of serotonin receptor ligand sufficient to reduce the pathological consequences of malarial infection in said patient, wherein said serotonin receptor ligand is characterized by having tbe ability to displace an identifying ligand that defines the serotonin receptor subtype 5HT1a or 5HT2/5HT1c and a serotonin receptor binding affinity constant ($K_i$) value of less than 410 nM.

2. A method of treating malaria in a patient in need thereof, said method consisting essentially of administering to said patient a therapeutically effective amount of serotonin receptor ligand, other than verapamil, sufficient to reduce the pathological consequences of malarial infection in said patient, wherein said serotonin receptor ligand is characterized by having the ability to displace an identifying ligand that defines the serotoriin receptor subtype 5HT1a or 5HT2/5HT1c.

3. A method of treating malaria in a patient in need thereof, said method comprising administering to said patient a therapeutically effective amount of serotonin receptor ligand sufficient to reduce the pathological consequences of malarial infection in said patient, wherein said serotonin receptor ligand is characterized by having the ability to displace an identifying ligand that defines the serotonin receptor subtype 5HT1a or 5HT2/5HT1c, and wherein the serotonin receptor ligand is selected from the group consisting of:

(i) an amino tetralin having the general structure:

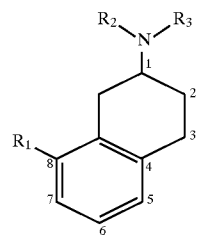

Wherein:

$R_1$=OH, O—$CH_3$, O—Ph, O-alkyl or O-aryl groups;
$R_2$=H, O—$CH_3$, an aryl or alkyl group; and
$R_3$=H, an aryl or alkyl group, $(CH_2)_3$—Ph or phthalyl, (ii) 8-hydroxy-N-di-n-propylaminotetralin (DPAT), (iii) a phenyl dioxin having the structure:

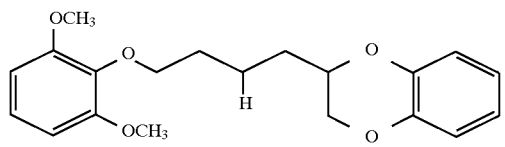

(iv) an ergoline having the general structure:

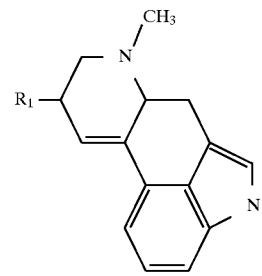

Wherein:

$R_1$=diethylamide, N—(C=O)—N(Et)$_2$, or N—(C=O)—O—$CH_2$—Ph, (v) an indole derivative having the general structure:

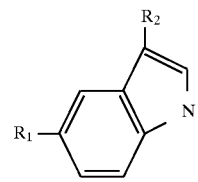

Wherein:

$R_1$ = O—$CH_3$ and

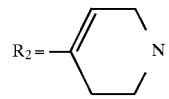

(vi) an alkylpiperidine having the general structure:

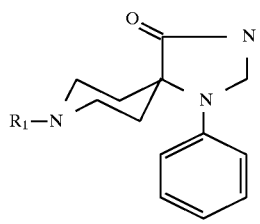

Wherein:

R$_1$=a benzalkylparafluoro or a 7-benzodioxin group.

4. The method of claim 3, wherein the patient is an animal susceptible to malaria.

5. The method of claim 4, wherein the patient is a mammal.

6. The method of claim 4, wherein the patient is a human.

7. The method of claim 3, wherein the serotonin receptor ligand is administered orally.

8. The method of claim 3, wherein the serotonin receptor ligand is administered by injection.

9. The method of claim 3, wherein the serotonin receptor ligand is the amino tetralin identified in (i).

10. The method of claim 3, wherein the serotonin receptor ligand is 8-hydroxy-N-di-n-propylaminotetralin (DPAT).

11. The method of claim 3, wherein the serotonin receptor ligand is the phenyl dioxin identified in (iii).

12. The method of claim 3, wherein the serotonin receptor ligand is the ergoline identified in (iv).

13. The method of claim 3, wherein the serotonin receptor ligand is the indole derivative identified in (v).

14. The method of claim 3, wherein the serotonin receptor ligand is the alkylpiperidine identified in (vi).

* * * * *